(12) United States Patent
Landau et al.

(10) Patent No.: US 6,783,509 B1
(45) Date of Patent: Aug. 31, 2004

(54) SINGLE-USE NEEDLE-LESS HYPODERMIC JET INJECTION APPARATUS AND METHOD

(75) Inventors: Sergio Landau, Laguna Niguel, CA (US); James M. Bonicatto, Portland, OR (US); Robert A. Miller, Portland, OR (US)

(73) Assignee: Bioject Inc., Tualatin, OR (US)

( * ) Notice: Subject to any disclaimer, the term of this patent is extended or adjusted under 35 U.S.C. 154(b) by 0 days.

(21) Appl. No.: 09/661,135

(22) Filed: Sep. 13, 2000

Related U.S. Application Data

(63) Continuation-in-part of application No. PCT/US00/03938, filed on Feb. 16, 2000, which is a continuation of application No. 09/252,131, filed on Feb. 18, 1999, now Pat. No. 6,264,629, and a continuation-in-part of application No. 09/195,334, filed on Nov. 18, 1998, now Pat. No. 6,096,002.

(51) Int. Cl.[7] .......................... H61M 5/30; H61M 37/00
(52) U.S. Cl. ......................................... 604/70; 604/143
(58) Field of Search .............................. 604/68–72, 140, 604/141, 143, 147, 131, 187, 148

(56) References Cited

U.S. PATENT DOCUMENTS

| | | |
|---|---|---|
| 2,653,602 A | 9/1953 | Smoot |
| 2,680,439 A | 6/1954 | Sutermeister |
| 3,115,133 A | 12/1963 | Morando |
| 3,292,621 A | 12/1966 | Banker |
| 3,561,443 A | 2/1971 | Banker |
| 3,688,765 A | 9/1972 | Gasaway |
| 3,695,266 A | 10/1972 | Lussier |
| 3,714,943 A | 2/1973 | Yanof et al. |
| 3,853,125 A | 12/1974 | Clark et al. |
| 3,945,379 A | 3/1976 | Pritz et al. |
| 4,059,107 A | 11/1977 | Iriguchi et al. |
| 4,596,556 A | 6/1986 | Morrow et al. |
| 4,680,027 A | 7/1987 | Parsons et al. |
| 4,717,384 A | 1/1988 | Waldeisen |
| 4,790,824 A | 12/1988 | Morrow et al. |
| 4,913,699 A | 4/1990 | Parsons |
| 4,940,460 A | 7/1990 | Casey, I. et al. |
| 5,009,637 A | 4/1991 | Newman et al. |
| 5,024,656 A | 6/1991 | Gasaway et al. |
| 5,383,851 A | 1/1995 | McKinnon, Jr. et al. |
| 5,503,627 A | 4/1996 | McKinnon et al. |
| 5,730,723 A | 3/1998 | Castellano et al. |
| 5,993,412 A | 11/1999 | Deily et al. |
| 6,096,002 A | 8/2000 | Landau |
| 6,132,395 A | 10/2000 | Landau et al. |
| 6,210,359 B1 | 4/2001 | Patel et al. |
| 6,264,629 B1 | 7/2001 | Landau |

FOREIGN PATENT DOCUMENTS

| | | |
|---|---|---|
| WO | WO00/33899 | 6/2000 |
| WO | WO00/48654 | 8/2000 |

*Primary Examiner*—Michael J. Hayes
(74) *Attorney, Agent, or Firm*—Kolisch Hartwell, P.C.

(57) ABSTRACT

A needleless injector system including: a first injector assembly; a gas capsule disposed within the first injector assembly and containing pressurized gas, with a pierceable surface at the forward end thereof to provide an injection source; a gas capsule piercing member disposed within the first injector assembly, where the piercing member and the gas capsule are movable relative to each other; a second injector assembly containing a medical treatment fluid and having a forward facing injection orifice for injecting the medical treatment fluid into a patient; and a resilient seal mounted between the gas capsule and the first injector assembly to contain all pressurized gas within a forward end of the first injector assembly after pressurized gas is released from the gas capsule following piercing of the gas capsule, in order to cause an immediate increase in pressure in the medical treatment fluid contained within the second injector assembly.

6 Claims, 11 Drawing Sheets

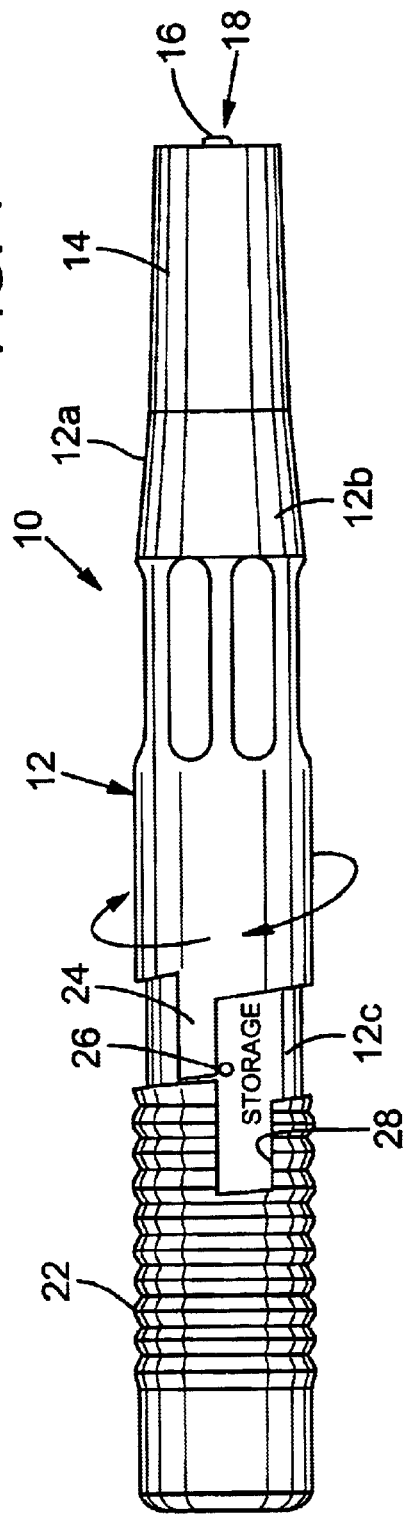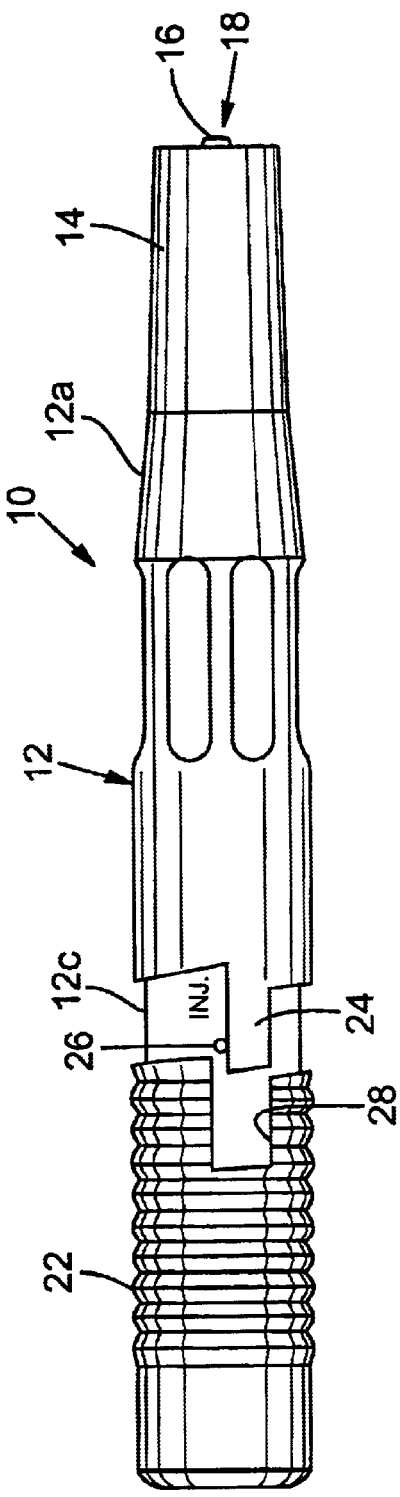

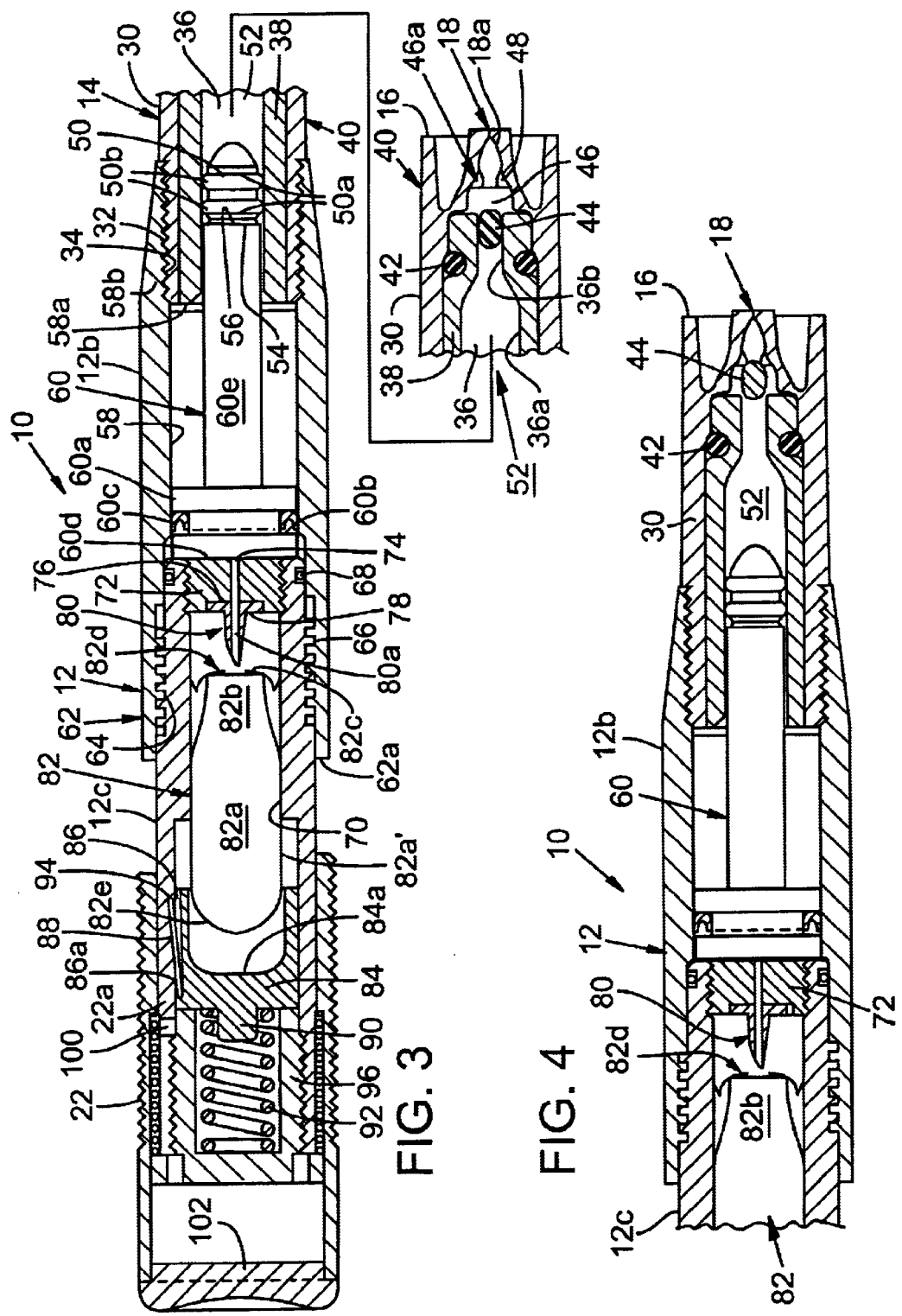

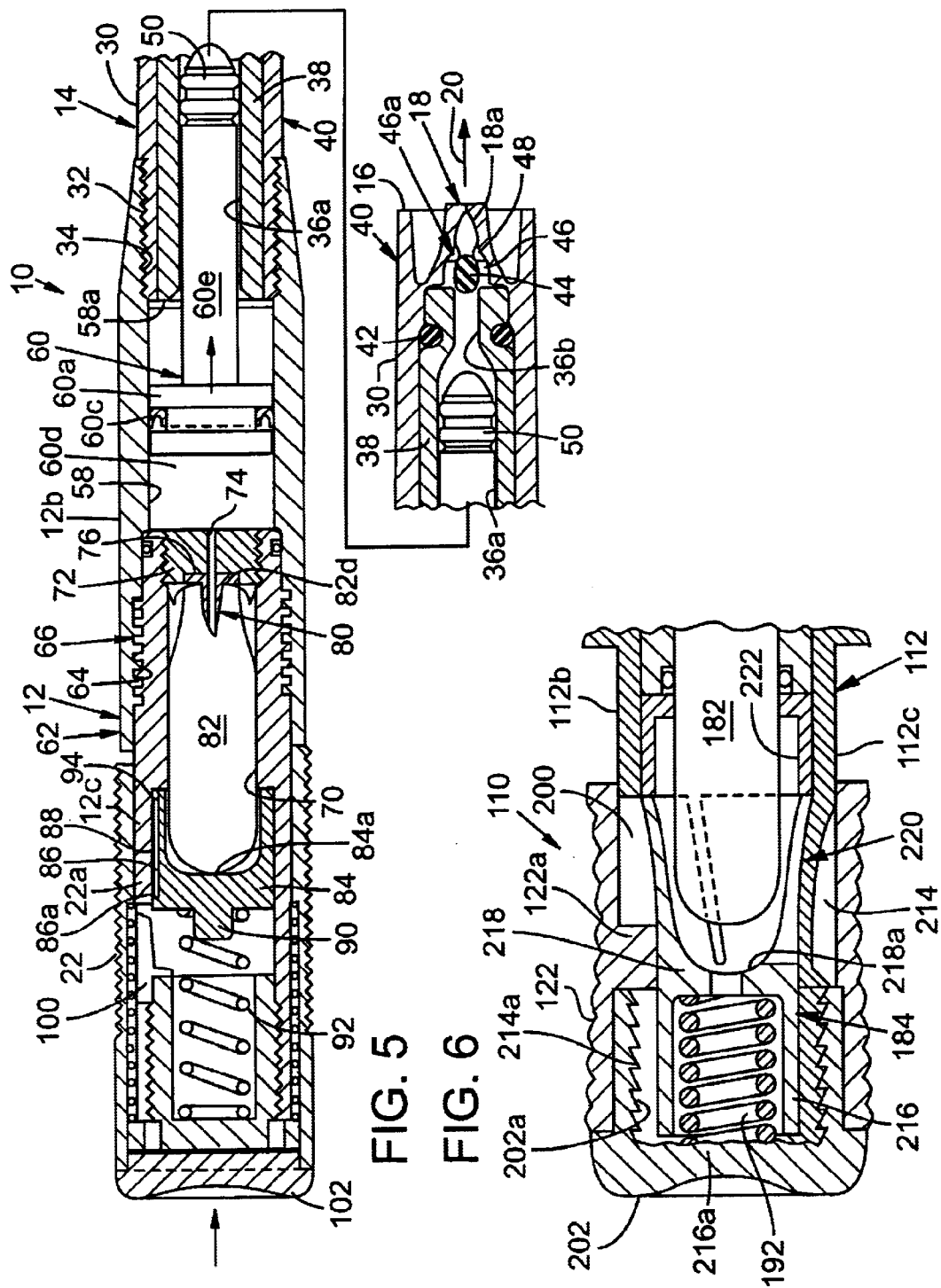

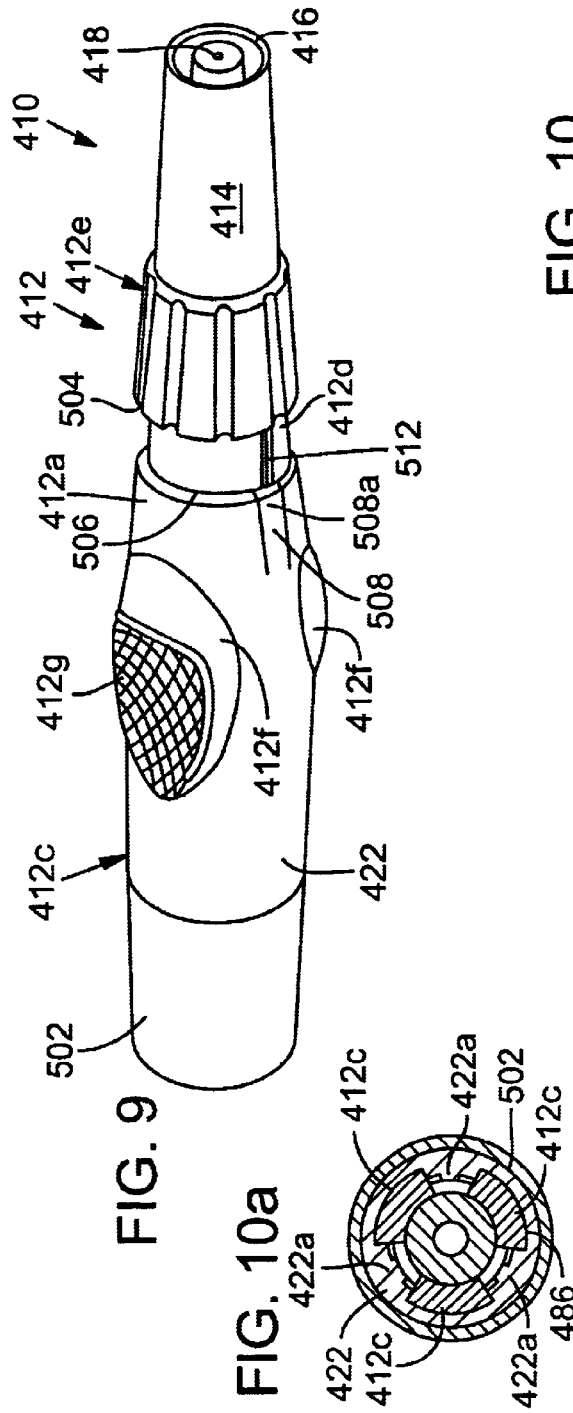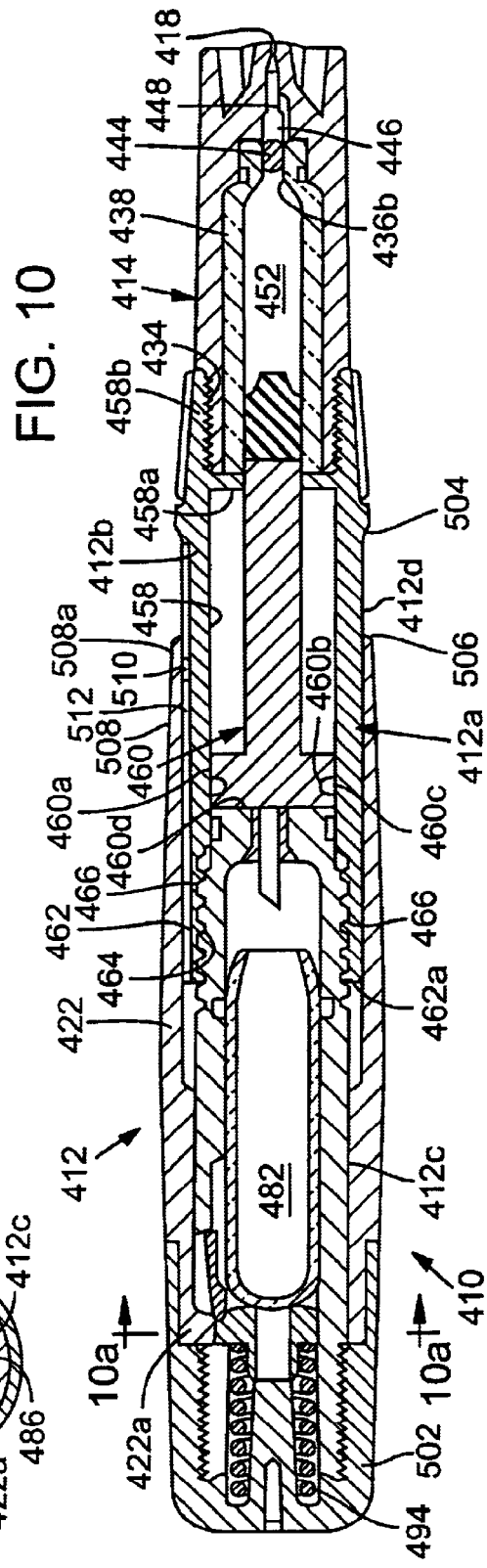

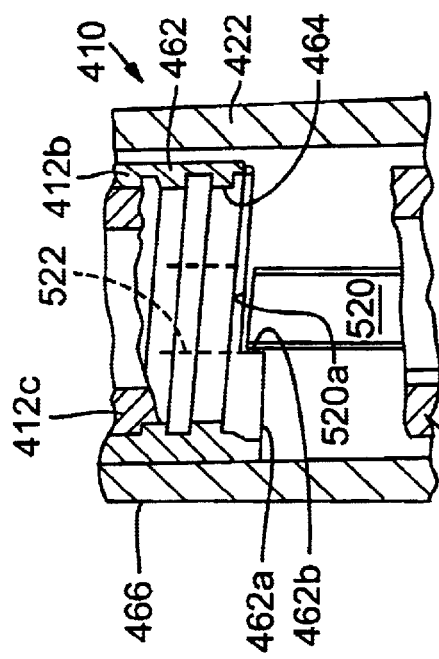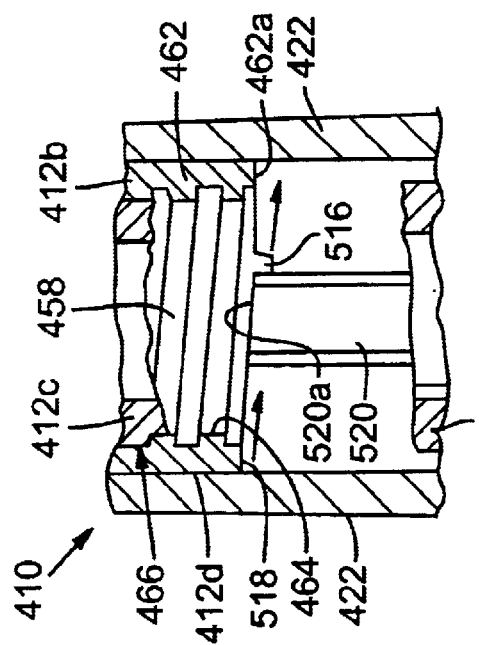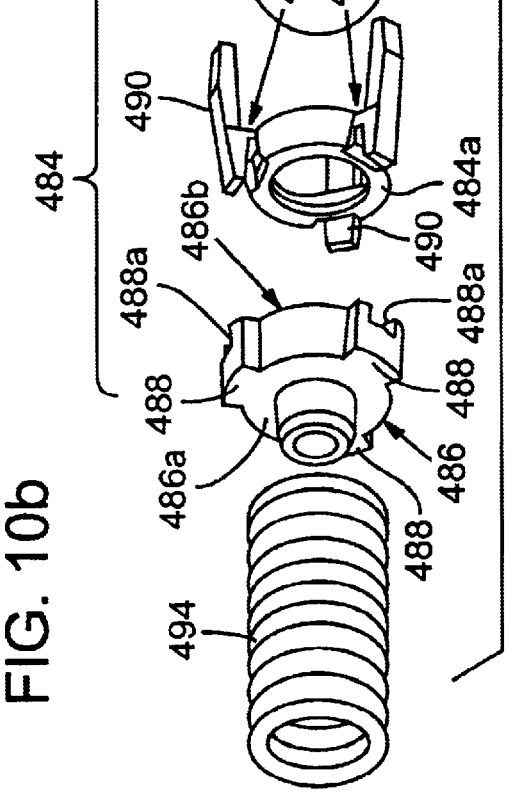

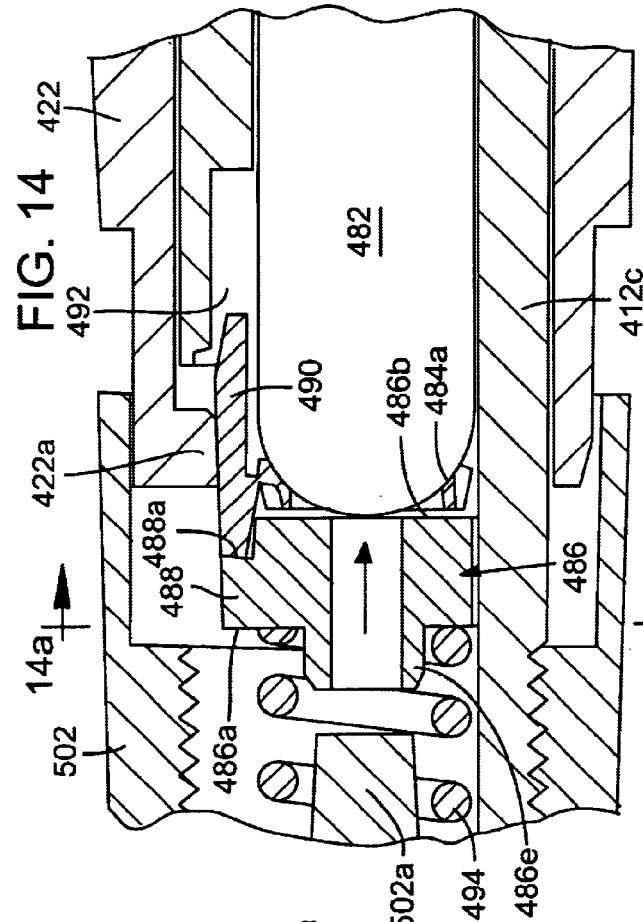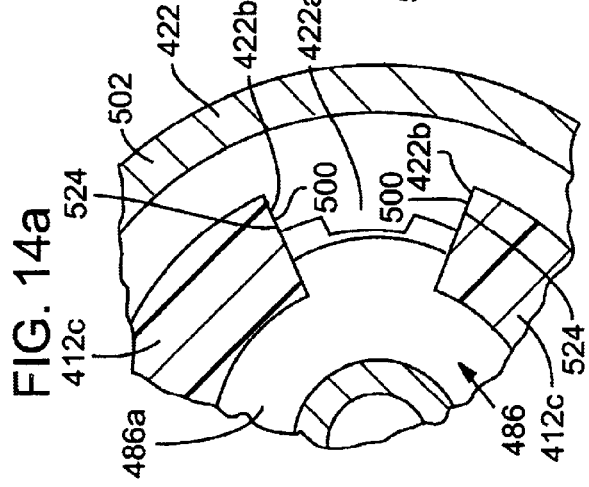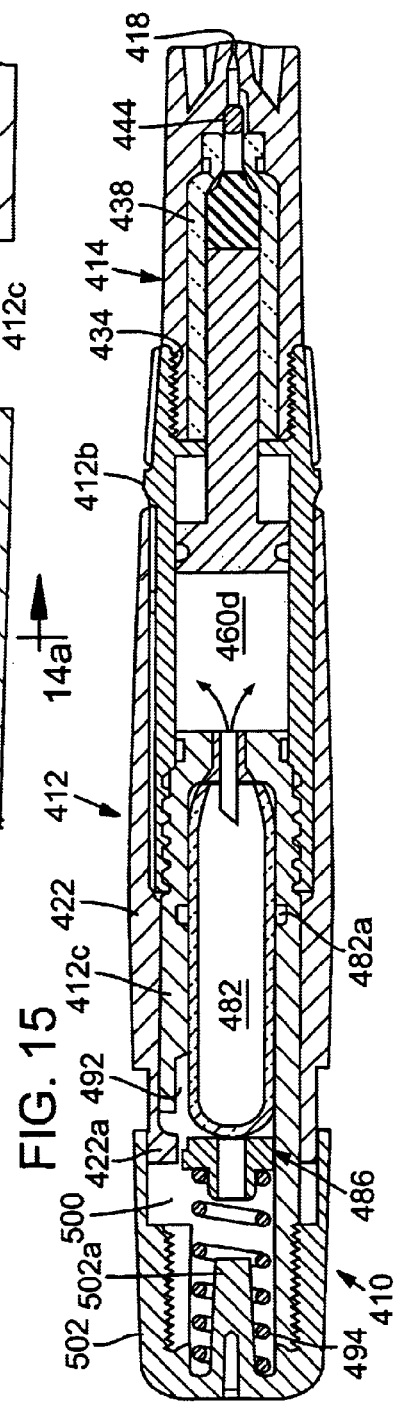

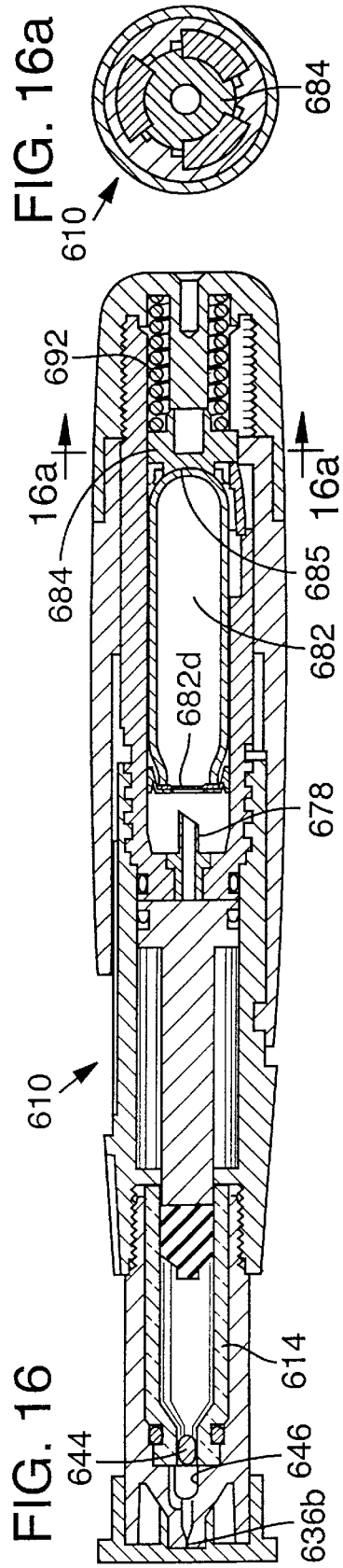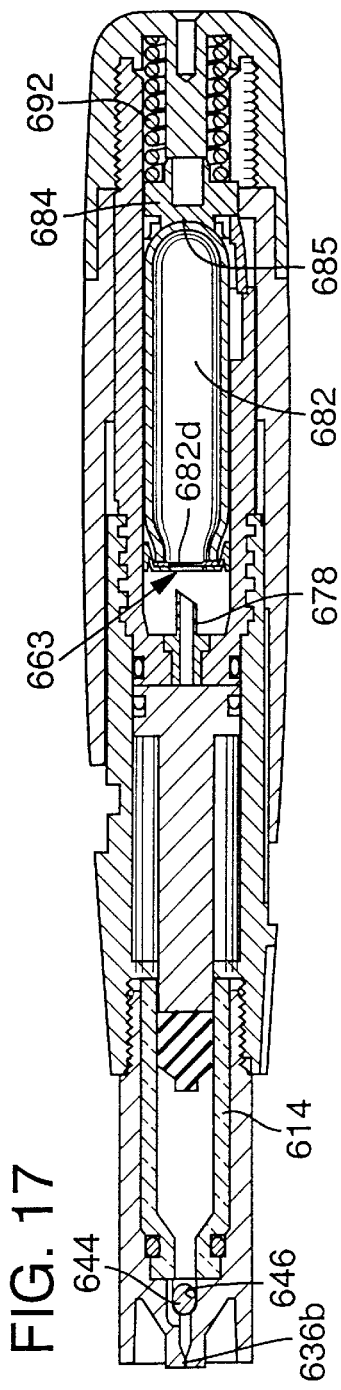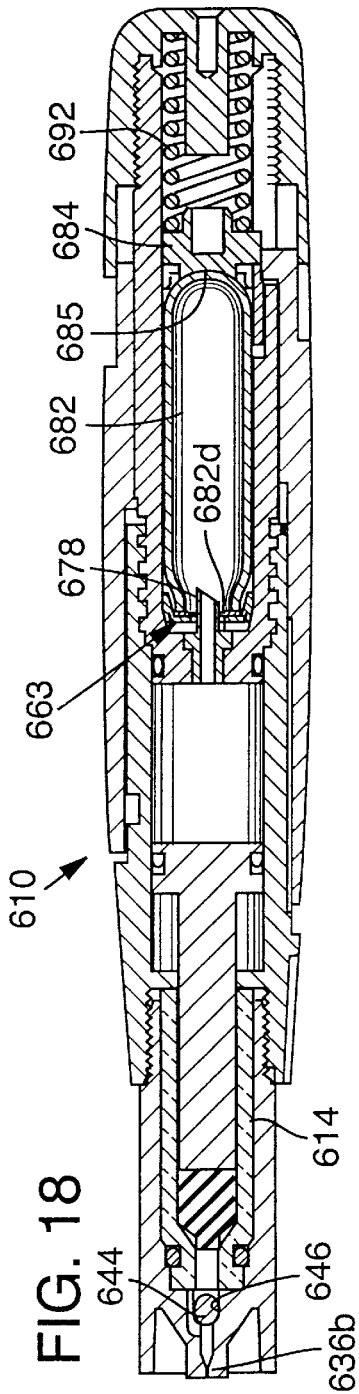

SINGLE-USE NEEDLE-LESS HYPODERMIC
JET INJECTION APPARATUS AND METHOD

CROSS REFERENCE TO RELATED
APPLICATION

This application is a continuation-in-part of United States Patent Application Ser. No. PCT/US/00/03938, filed Feb. 16, 2000, which is a continuation-in-part of U.S. patent application Ser. No. 09/195,334, filed Nov. 18, 1998, now U.S. Pat. No. 6,096,002 a continuation of U.S. patent application Ser. No. 09/252,131, filed Feb. 18, 1999, now U.S. Pat. No. 6,264,629.

BACKGROUND OF THE INVENTION

1. Field of the Invention

The present invention relates generally to a single-use disposable needle-less (or needle-free) jet injection device. Particularly, this invention relates to such a jet injection device which comprises a hand-held injector having a pre-filled drug cartridge sealingly carrying injectable medication, a sealed cylinder of pressurized gas, a pre-energized discharge mechanism for penetrating the gas cylinder, and a trigger device for releasing the discharge mechanism. Features are provided which simultaneously unseal the drug cartridge and prepare the device for performing a jet injection when a user of the device changes it from a storage configuration to a use configuration. When the user actuated the injection device, the trigger device releases the discharge mechanism to penetrate the gas cylinder, which drives a piston of the drug cartridge to effect a hypodermic jet injection.

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued Jun. 24, 1986 to J. Thomas Morrow, et al.; U.S. Pat. No. 4,913,699; issued Apr. 3, 1990 to James S. Parsons; and U.S. Pat. No. 5,730,723, issued Mar. 24, 1998, to Thomas P. Castellano, et al. WIPO publication WO 97/37705 also discloses a gas powered disposable needle-less hypodermic jet injector.

The Morrow, et al. '556 patent is believed to teach a reusable hypodermic jet injection device in which a housing receives a shell or cartridge having a bore leading to a discharge aperture. Within the bore is received both a plunger sealingly engaging the bore, and a pressurized gas cylinder which rests against the plunger. The injection device includes a ram which has a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger, and spent gas cylinder, is discarded after an injection; and a new shell pre-filled with medication and with a new gas cylinder is used for each injection.

The Parsons '699 patent is believed to teach a single-use jet injector which is totally discarded after one use. This injector is believed to have a body with a pair of gas chambers separated by a breakable valve. One of the gas chambers contains a pressurized gas, while the other chamber is sealingly bounded by a piston which drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thornlea, is believed to disclose a disposable hypodermic jet injector in which the device is powered by a gas pressure spring of the type common in the tool and die art as a substitute for the conventional metal spring-powered ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice in order to produce a jet hypodermic injection from liquid held in the bore ahead of the piston.

The Weston device is thought to have several deficiencies: such as difficult and costly manufacturing and sterilization processes, because pressurized gas and a drug dose need to be contained in the same package; and including a possible inability to endure long-term storage while still retaining the gas pressure in the gas spring to power an injection, and also maintaining the medication integrity. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

SUMMARY OF THE INVENTION

In view of the above, it is desirable and is an object for this invention to provide a needle-less hypodermic jet injection device which reduces the severity of or avoids one or more of the limitations of the conventional technology.

Thus, it is an object of this invention to provide a single-use, disposable, needle-free gas-powered hypodermic jet injector utilizing a pressurized gas source which is hermetically sealed until the moment of injection.

Further, an object of this invention is to provide such a gas powered jet injector in which the device has a storage configuration and a use configuration. In the storage configuration, the device is safe, with the drug cartridge sealed closed, and is incapable of effecting a jet injection. In the use configuration, the device is prepared for making a jet injection, with the drug cartridge opened in preparation for this injection.

Additionally, an object for this invention is to provide such an injection device having a multi-function component which alternatively maintains the injector in a safe storage condition, and also allows a user to place the injection device into a use condition preparatory for performing a jet injection. When the user places the device into the use configuration, the multi-function component prepares the jet injection device by effecting unsealing of the previously sealed drug cartridge, and also removes a safety block from an obstructing position relative to a trigger of the device. Thereafter, the trigger of the injector can be manually activated by a user of the device to perform an injection.

Accordingly, a needle-less hypodermic jet injection system embodying this invention includes, for example: a hand piece assembly having a body including a drug injection cartridge with a medication cylinder pre-filled with substantially incompressible liquid medication such that substantially no ullage volume exists in the medication cylinder, the medication cylinder leading to an outlet orifice a plug-capture chamber and a drug injection nozzle, a sealing member sealingly and movably received in the outlet orifice, and a drug-injection piston; the hand piece assembly further defining a first bore within the body for movably receiving a gas-power piston, a gas power piston movably received in the first bore and having a ram portion extending into the drug injection cartridge to abut with the drug-injection piston, the body and gas-power piston cooperating to define a first variable-volume chamber in the first bore; the body also defining an elongate second bore in gas communication with the first bore and separated therefrom by a center wall portion of the body, a cylindrical gas capsule received into the second bore, the gas capsule having a penetrable wall section disposed toward the center wall, the center wall carrying a penetrator disposed toward the penetrable wall section of the gas capsule, and the hand piece assembly carrying a discharge mechanism including a trigger member outwardly disposed on the body and a hammer movable in the body in response to actuation of the trigger to forcefully move the gas capsule in the second bore so as to impale the gas capsule at the penetrable wall section thereof upon the penetrator and thus to communicate pressurized gas to the first chamber; whereby, the pressurized gas in the first chamber drives the gas-power piston to effect a hypodermic jet injection from the drug injection cartridge, and the body and trigger member cooperatively defining a first relative position in which the ram portion confronts but does not displace the injection piston so that the sealing member is disposed in the outlet orifice to maintain the drug injection cartridge sealingly closed, and the body and trigger member in a second relative position preparatory to effecting a jet injection causing the ram portion to abut and move the drug injection piston to a second position displacing the drug injection piston to a second position so that the sealing member is displaced from the outlet orifice into the plug-capture chamber by the liquid medication and unseals the drug injection cartridge.

According to a further aspect this invention provides: a needle-less hypodermic jet injection device comprising a pre-filled drug injection cartridge including a medication cylinder having an outlet orifice, an injection nozzle, a flow path communicating the outlet orifice to the injection nozzle, a plug member in a first position sealingly disposed in the flow path, a drug-injection piston in a first position cooperating with the medication cylinder to define a variable-volume chamber of first selected size, and a dose of substantially incompressible liquid medication substantially filling the variable-volume chamber at the first size with substantially no ullage volume. The drug-injection piston having a second position cooperating with the medication cylinder to define a variable-volume chamber of second selected size smaller than the first selected size, so that the incompressible liquid medication displaces the plug member from the first position of sealing disposition in the flow path to a second position of capture in the flow path, the medication cylinder and the plug member in the second position thereof cooperatively defining an open flow path between the variable-volume chamber and the injection nozzle. A hand piece assembly having a body holding the drug injection cartridge, the hand piece assembly including means for forcefully moving the drug injection piston from the second position to a third position so as to reduce the volume of the variable-volume chamber substantially ejecting the dose of liquid medication via the injection nozzle. The hand piece assembly further including a first body portion holding the drug injection cartridge, and an abutment member selectively movable into engagement with the drug injection piston to move the drug injection piston from the first position to the second position.

Additional objects and advantages of this invention will appear from a reading of the following detailed description of a single exemplary preferred embodiment, taken in conjunction with the appended drawing Figures, in which the same reference numeral is used throughout the several views to indicate the same feature, or features which are analogous in structure or function.

BRIEF DESCRIPTION OF THE DRAWINGS

FIG. 1 provides an exterior side elevation view of a single-use, needle-less hypodermic jet injector device embodying the present invention, and in which the device is in a "storage" configuration;

FIG. 2 is an exterior side elevation view of the injector device seen in FIG. 1, but with the device shown in an "inject" configuration preparatory to effecting a hypodermic jet injection;

FIG. 3 provides a longitudinal cross sectional view through the needle-less hypodermic jet injection device of FIG. 1, and shows the device in the "storage" configuration;

FIG. 4 is a fragmentary cross sectional view similar to FIG. 3, but shows the hypodermic jet injection device in the "inject" configuration;

FIG. 5 is also a fragmentary cross sectional view similar to FIGS. 3 and 4, but shows the hypodermic jet injection device during the process of effecting a jet injection;

FIG. 6 is a fragmentary cross sectional view similar to a portion of FIG. 4, but shows a respective portion of an alternative embodiment of a single-use, needle-less hypodermic jet injection device according to the present invention;

FIG. 9 provides an exterior side elevation view of an alternative embodiment of a single-use, needle-less hypodermic jet injector device embodying the present invention, and in which the device is in a "storage" configuration;

FIG. 10 provides a longitudinal cross sectional view through the needle-less hypodermic jet injection device of FIG. 9, and shows the device in the "storage" configuration;

FIG. 10a is a fragmentary cross sectional view taken along line a—a of FIG. 10;

FIG. 10b is a fragmentary longitudinal cross sectional view of a portion of the device of FIG. 10, with portions removed or broken away for clarity of illustration, with cooperating parts shown in their "storage" positions, and is shown at an enlarged size;

FIG. 12a is a fragmentary longitudinal cross sectional view similar to FIG. 10b, but with cooperating parts in their "inject" positions, and is also shown at the same enlarged size;

FIG. 13 provides an exploded perspective view of parts of the injection device of FIGS. 9–12;

FIG. 14 is a greatly enlarged fragmentary cross sectional view similar to a portion of FIG. 12, but shows the hypodermic jet injection device during the process of effecting a jet injection;

FIG. 14a is a fragmentary cross sectional view taken at plane 14a—14a of FIG. 14; and FIG. 15 is a longitudinal cross sectional view similar to FIGS. 10 and 12, but showing the device after completion of an hypodermic jet injection.

FIG. 16 is a side elevation sectional view of another embodiment of the invention, showing the device in the "storage" configuration;

FIG. 16a is an end elevation sectional view taken along line 16a—16a of FIG. 16.

FIG. 17 is a side elevation sectional view similar to FIG. 16, but showing the device in the "inject" configuration;

FIG. 18 is a side elevation sectional view similar to FIG. 16, but showing the device in the "fired" configuration;

DETAILED DESCRIPTION OF EXEMPLARY PREFERRED EMBODIMENTS OF THE INVENTION

Figure 7:
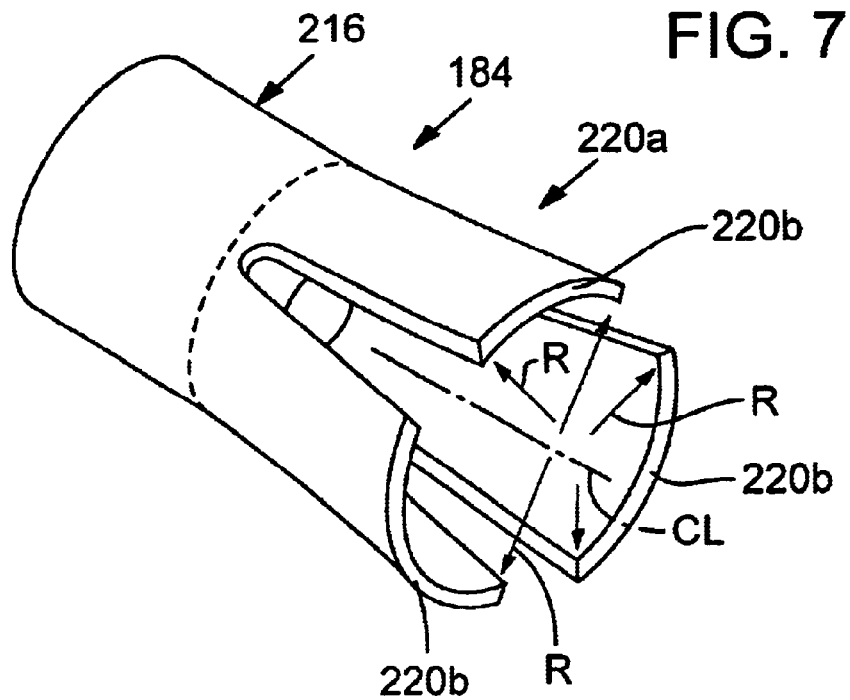
FIG. 7 is a perspective view of a portion of the device seen in FIG. 6.

Overview, Storage of the Device, and its Preparation for Effecting a Jet Injection Viewing FIG. 1, a needle-free, hypodermic jet injection device 10 is shown in a storage configuration in which it is maintained until it is prepared for its use in administering an injection. In this storage configuration, the device is incapable of effecting a jet injection, is safe, and can be stored for a comparatively long time while requiring only a moment of preparation before it can be used to make a jet injection of the medication within the device 10.

The storage configuration shown may be referred to as a locked configurations because in this configuration that device cannot administer an injection. As described below, the locking system that enables conversion from the locked, or storage configuration to the unlocked or injection configuration includes trigger sleeve 22 and projection 24 abutting trigger sleeve 22, relative rotation of a first portion 12b and a second portion 12c aligns projection 24 with recess 28 to permit relative axial movement between first portion 12b and second portion 12c. These parts define the locking system of device 10.

The device 10 includes a hand piece assembly 12, also known as a first injector assembly, preferably fabricated principally of injection molded plastic polymers, and with a body 12a including a pre-filled drug injection cartridge 14, also known as a second injector assembly. The word "drug" as used herein is intended to encompass, for example, and without limitation, any medication, pharmaceutical, therapeutic, vaccine, or other material which can be administered by jet injection. Essentially, such an injectable medication is in the form of a substantially incompressible liquid, and as will be seen, this liquid substantially fills the drug injection cartridge so that no ullage volume of compressible gas is present in this cartridge.

The pre-filled drug injection cartridge 14 has an end surface 16 at which is defined a fine-dimension injection orifice opening 18. When the device 10 is used to effect an injection, a high velocity jet of liquid medication issues from this orifice (as is indicated by arrow 20 of FIG. 5). To use the device 10, it is first placed in an "inject" configuration, the end surface 16 is pressed against the skin of a patient who is to receive the jet injection, and then the device 10 is triggered so that the jet 20 issues out and penetrates the skin. Thus, the liquid medication enters the tissues of the patient without the use of a hypodermic needle.

Placing the device 10 in the "inject" configuration is effected manually by a user of the device 10 who rotates a first portion 12b of the body 12a relative to a second portion 12c. As is seen in FIG. 1, the body portion 12c carries a trigger sleeve 22, while the portion 12b carries a projection 24 abutting this sleeve. The projection 24 and a blocking pin 26 cooperate to prevent the body portions 12b and 12c from being relatively rotated except in the direction of the arrow of FIG. 1. When a user effects this relative rotation of the body portions 12b and 12c through a rotation of almost 360°, then this relative rotation aligns the projection 24 with a recess 28 on the trigger sleeve 22, reveals the abbreviation of the word "inject" (indicated on FIG. 2 by the letters "INJ") on the body portion 12c.

This relative rotation of the body portions 12b and 12c also effects a selected relative axial movement of these body portions toward one another (as will be further described below), and places the device 10 in the "inject" configuration seen in FIG. 2. In this "inject" configuration, the device 10 is positioned with its surface 16 against the skin of the person who is to receive the injection, and an axial pressure is applied to the trigger sleeve 22. The trigger sleeve 22 moves axially along the body portion 12c, and this movement triggers the device 10 to effect injection jet 20 (recalling FIG. 5).

Structure of the Device 10

Turning now to FIGS. 3, 4, and 5, in conjunction with one another, FIG. 3 shows the device 10 in the storage configuration of FIG. 1 preparatory to giving an injection. In FIG. 4 shows the device in the "inject" configuration, and FIG. 5 shows the device during the brief interval of an injection. In these Figures, it is seen that the drug cartridge 14 includes a cylindrical body 30 defining an external thread section 32. This external thread 32 is threadably received by a matching internal thread section 34 of the body portion 12b. Preferably, a thread locking compound, such as an anaerobic adhesive, is applied to the threads 32 of the cartridge 14 when it is assembled to the body portion 12b during manufacture of the device 10. Alternatively, a self-locking thread design or a thread-locking feature may be used on the device 10 to prevent the drug injection cartridge 14 from being removed from the device 10. Thus, the cartridge is not removable from the device 10, and the device 10 and cartridge 14 are disposed of after the first and only injection effected with the device 10.

An advantageous feature of the device 10 embodying the present invention, and one which results from this construction of the device, is that the injection cartridge 14 may be manufactured and filled at a drug company (without the drug manufacturer having to be concerned with handling capsules of pressurized gas), the gas pressure capsule of the device may be manufactured and filled at a factory devoted to this item (without this manufacturer having to handle drugs), and the hand piece assembly of the device may be manufactured at yet another location, if desired. Subsequently, completion of the device 10 requires merely the combining of the hand piece assembly, gas capsule, and drug injection cartridge.

The body 30 of cartridge 14 defines a stepped through bore 36 having a larger diameter portion 36a which extends substantially the length of the body 26. Adjacent to the forward end of the body 30 (i.e., adjacent to the end defining surface 16), the bore 36 steps down and defines an outlet orifice 36b. It is seen that the bore portion 36a and outlet orifice 36b are defined by a glass sleeve 38 which is received into a molded plastic body 40. An O-ring type of seal member 42 prevents leakage between the glass sleeve 38 and the body 40.

As those who are ordinarily skilled in the pertinent arts will understand, many medications are not suitable for long-term storage in contact with plastics, but will store satisfactorily in contact with glass. Thus, this construction of the cartridge 14 makes it suitable for long-term storage of even medications of this nature. However, for medications that will store satisfactorily in contact with plastic polymers, this construction detail is optional and the entire injection cartridge body 30 may be formed of a selected polymer.

In the embodiment of cartridge 14 having the glass sleeve 38, the outlet orifice 36b is sealingly closed in the storage configuration of the device 10 by a plug 44. Importantly, viewing FIGS. 3–5, it is seen that the cartridge 14 defines a plug-capture chamber 46 immediately outside of the outlet orifice 36b (i.e., rightwardly of this outlet orifice, viewing FIGS. 3–5). The plug capture chamber 46 includes a radial array 46a of individual radially inwardly and axially extending ribs 48 disposed in a spaced relation to the outlet orifice 36b. These ribs 48 are arrayed radially about and in a transition bore portion 18a leading to the injection orifice 18. Thus, as will be seen, the plug member 44 can be received into the plug-capture chamber 46 and be supported on the ribs 48 without it blocking the injection orifice 18.

Sealingly and movably received in the bore section 36a is a resilient piston member 50. This piston member defines multiple circumferential grooves 50a interdigitated with sealing ribs 50b. The sealing ribs 50b sealingly and movingly engages the bore 36a of the injection cartridge (i.e., with the bore 36a of glass sleeve 38 in this case). The piston member 34 and body 30 cooperatively define a medication chamber 52 communicating outwardly of the cartridge 14 via the injection orifice 18. Prior to its use to effect an injection, the orifice 18 of each fresh and pre-filled device 10 will ordinarily also be sealed by an adhesively-applied, peel-off type of sealing membrane, which may be formed, for example, of foil or of a polymer/paper laminate. Such peel-off seals are conventional and well known, and for this reason, the seal formerly on cartridge 14 of device 10 as seen in FIG. 3 is not shown in the drawing Figures.

Further considering the cartridge 14, it is seen that the piston member 50 defines an abutment surface 54 confronting the opening of bore 36 on body 30. This abutment surface 54 is abutted by an end surface 56 on an injection ram of the hand piece assembly 12 (which injection ram will be further described below). In the storage configuration of the device 10, the end surface 56 confronts piston 50, but does not displace it from the position seen in FIG. 3. In this storage configuration of the device 10, the chamber 52 is sealed and is substantially full of incompressible liquid, without any substantial ullage volume of compressible gas being in the chamber 52. The injection ram will be understood as effective during a jet injection to forcefully move the piston 50 inwardly of the bore section 36a toward the outlet orifice 36b.

Hand Piece Assembly 12

Considering now the hand piece assembly 12 in greater detail, as seen in FIGS. 1–5, it is seen that the body 12a generally is formed of two main cooperative tubular sections 12b and 12c, which are threadably engaged with one another to form the hand piece assembly 12. Preferably both of the body sections 12b and 12c, as well as other components of the device 12 not otherwise identified as being made of some other material, are all formed of plastic polymers. Further, the preferred process for making the device 10 is by injection molding of the components formed of plastic polymer, so that manufacturing cost are very low. Materials utilization for the device 10 is very small as well, so that disposing of the device after a single injection does not cause a serious environmental concern.

The forward tubular body section 12b defines a stepped through bore 58, a forward portion 58a of which opens at 58b forwardly on the body 12, and which inwardly of this bore opening 58a defines the internal thread section 34 for threadably receiving the external threads 32 on the drug cartridge 14. Sealingly and movably received in the bore portion 58a is a stepped injection piston member 60. A larger diameter portion 60a of this piston member defines a groove 60b carrying a seal member 60c. The seal member 60c movingly engages sealingly with the bore portion 58a and bounds a gas pressure chamber 60d, which is to the left of this piston member as seen in FIGS. 3, 4, and 5. It is to be noted that in FIGS. 3 and 4, this chamber 60d is at a minimal volume, and so the lead line from reference numeral 60d extends into the interface of the piston member 60 with the housing portion 12c.

A smaller diameter portion 60e of the piston member 60 is elongated and extends in the bore 58 to also be received into the bore portion 36a of the drug cartridge 14, as is seen in FIG. 3 in the storage configuration of the device 10. The piston portion 60e defines the end surface 56 which confronts and abuts the surface 54 of the piston member 50 of a drug cartridge 14. Thus, the piston portion 60e provides the injection ram of the device 10.

Considering the forward body section 12b in still greater detail, it is seen that this body section defines a tubular aft body section 62. This aft body section includes an axially disposed end surface 62a at which the stepped through bore 58 opens, and which defines an internal thread section 64 threadably engaging onto matching threads 66 of body section 12c. For purposes of explanation, and without limitation of the present invention, the threads 64 and 66 may have a pitch of about 14 threads per inch.

As is seen comparing FIGS. 1 and 2, the device 10 is converted from its storage to its "inject" configuration by rotating the body portions 12b and 12c in a relative rotational direction that threads these body portions together along threads 64 and 66. As was explained above, this relative rotation of the body sections 12b and 12c brings projection 24 into alignment with recess 28 on trigger sleeve 22, and makes possible the subsequent triggering of the device 10.

Still considering FIGS. 2 and 3, it is seen that the aft body portion 12c outwardly defines the thread section 66 and slidably carries the trigger sleeve 22. Adjacent to the thread section 66, the body portion 12c carries an O-ring type of sealing member 68 which sealingly engages the body portion 12b both when the body portions are in their "storage" relative configuration of FIG. 3, and also when these body portions are in their "inject" relative positions as is seen in FIGS. 4 and 5.

Body portion 12c defines a stepped through bore 70 which is substantially closed at the end of this bore adjacent to the forward body portion 12b by a wall member 72. This wall member 72 defines a stepped through bore 74 in a larger diameter part of which is seated a disk part 76 of a penetrator member 78. This penetrator member 78 includes a hollow penetrator spike 80 which itself has a bore 80a communicating through the wall member 72 via the smaller diameter portion of bore 74. Thus, the bore 70 is communicated to the chamber 60d adjacent to injection piston 60 in the body portion 12b.

Slidably received in the bore 74 adjacent to and confronting the penetrator member 78 is a gas pressure capsule 82. This gas pressure capsule 82 includes a body 82a, having a cylindrical outer wall portion 82a'. The capsule 82 is also tapered down at a forward end to provide a reduced diameter portion 82b leading to an axially disposed end surface 82c defined by a penetrable wall section 82d (the wall section being indicated by the arrowed numeral in FIG. 3). The gas capsule 82 is preferably formed of metal, and contains a supply of pressurized gas. Because the pressurized gas is contained in the capsule 82 until the moment of injection, the plastic parts of the device 10 are not exposed to or stressed by this pressurized gas until an injection is effected using the device 10. For this reason, the device 10 is believed to have a much more reliable storage life than prior devices which attempt to contain pressurized gas in a plastic or plastic-composite containment.

Gas capsule wall section 82d confronts and is spaced slightly from the penetrator spike 80. At an opposite or rearward end of the capsule 82, the capsule defines an outwardly rounded end wall 82e.

Also slidably received into the bore 70 and confronting the end 82e of capsule 82 is tubular and cylindrical hammer member 84. This hammer member 84 defines an end surface 84a which is engageable with the surface 82e of capsule 82, an axially extending groove 86 having an end wall at 86a (into which a dowel pin 88 is received), and an axial protrusion at 90 which serves to center a spring 92.

The dowel pin 88 is engaged in a first position (i.e., in the "storage" configuration of the device 10) at end 86a of groove 86, and the other end of this pin rests upon a metal (i.e., preferably hardened steel) sear pin 94 carried by the body portion 12c. Thus, as is seen in FIGS. 3 and 4, the hammer 84 is maintained in a "cocked" position with the spring 92 pre-loaded between the hammer 84 and a spring seat member 96 threadably engaging into the end of body portion 12c.

In order to provide for movement of the trigger sleeve 22 to effect release of the hammer 84, the body portion 12c defines an axially extending slot 100, and the trigger sleeve 22 carries a radially inwardly extending trigger block 22a, which is slidably received in this slot 100 and which confronts the dowel pin 88, as is seen in FIG. 3. Also, an end cap 102 is adhesively retained onto the trigger sleeve 22 and closes the end of this trigger sleeve so that a user's thumb, for example, may be used to effect forward movement of the trigger sleeve when an injection is to be effected. It will be understood that the trigger sleeve 22 may alternatively be grasped between the thumb and fingers, for example, to position the device 10 for making an injection, and then effecting forward movement of the trigger sleeve 22 to effect this injection. However, as was pointed out above in connection to the comparison of FIGS. 1 and 2, the device 10 is first placed by a user into its "inject" configuration before a jet injection can be effected. This conversion of the device 10 from its "storage" configuration to its inject configuration is effected by relative rotation of the body portions 12b and 12c, as is indicated by the arrow on FIG. 1. As is seen in FIG. 2, this relative rotation of the body portions 12b and 12c brings the projection 24 into engagement with blocking pin 26 and into alignment with recess 28, so that the trigger sleeve 22 is movable in the axial direction toward body portion 12b. However, viewing FIG. 4, it is seen that this relative rotation of the body portions 12b and 12c also threads body portion 12c by substantially one thread pitch dimension into the body portion 12b.

Because the body portion 12c and wall member 72 are abutting injection piston member 50, this piston member 50 is moved rightwardly, viewing FIG. 4, by substantially one thread pitch dimension. Consequently, the ram portion 60e of the injection piston 60 moves forward and forces piston 50 forwardly by a sufficient amount that plug member 44 is dislodged hydraulically (recalling that the liquid medication in chamber 52 is substantially incompressible) from the outlet orifice 36b and into plug-capture chamber 46. In this chamber 46, the plug member 44 is retained and rests upon the ribs 48 while these ribs provide a flow path leading around the plug member 44 from the outlet orifice 36b to the injection orifice 18.

Although the conversion of device 10 from its "storage" configuration to its "inject" configuration unseals the injection cartridge 14, this is not detrimental to the integrity of the medication in chamber 52 because it happens mere moments before the device 10 is used to inject the medication into a patient. This injection is effected by placement of the device 10 with its surface 16 against the skin at the intended location of injection, and sliding of trigger sleeve 22 forward (which also assists in seeing that the device 10 is held firmly to the skin), so that the trigger block 102 slides along slot 100 to dislodge the dowel pin 88 from sear pin 94, viewing FIG. 5.

As is seen in FIG. 5, the result is that the hammer member 84 is driven forward by spring 92, impacts the capsule 82, and impales this capsule at penetrable wall 82d, as is seen in FIG. 5. The result is the penetrator spike 80 penetrates the wall 82c of the capsule 82, and allows pressurized gas from this capsule to flow along the bores 80a and 74 into the chamber 60d. This pressurized gas in chamber 60d drives piston member 60 forwardly, so that the piston 50 in bore 36a is also driven forwardly. Forward movement of piston 50 drives the liquid medication out of chamber 52, past the plug member 44 in plug-capture chamber 46, and out of injection orifice 18, forming injection jet 20.

After the jet injection depicted in FIG. 5, the device 10 is disposed of by the user of the device, and it is not again used. That is, the device 10 is a single-use device and is not designed or intended to be recharged or refilled. This design of the device 10 insures safety for those receiving an injection by use of the device 10 because they can be sure that only a new and never before used device is used to give them the injection. Further, the device 10 provides for a long-term storage of the device and its pre-filled medication, so that devices 10 may be stockpiled in anticipation of such events as mass inoculations. The device 10 may be used under exigent circumstances as well, since it requires only a few seconds or less to convert it from its "storage" configuration to its "inject" configuration, after which the jet injection is immediately effected.

FIG. 6 provides a fragmentary view of an alternative embodiment of the jet injection device according to this invention. In FIG. 6, only the aft or trigger assembly end of the device is illustrated. The forward end of the device and its pre-filled medication injection cartridge may be substantially as depicted and described above. Because the device illustrated in FIGS. 6–8 has many features that are the same as, or which are analogous in structure or function to those illustrated and described above, these features are indicated on FIGS. 6–8 using the same reference numeral used above, and increased by one-hundred (100).

Figure 8:
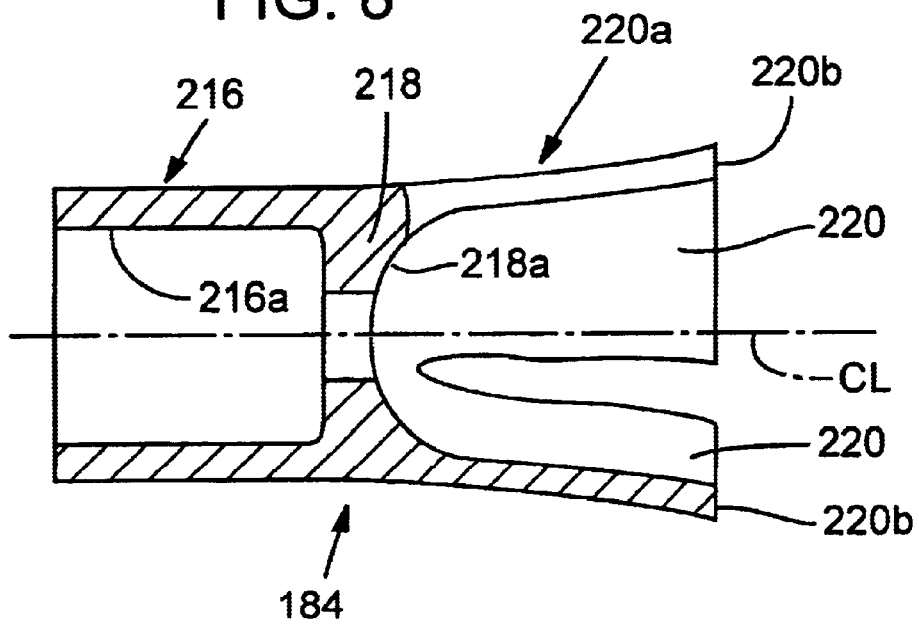
FIG. 8 provides a cross sectional view of the portion of the device seen in FIG. 7.

Viewing FIGS. 6–8 in conjunction with one another, it is seen that the injection device 110 includes a body portion 112c, which is necked to a slightly smaller diameter aft portion at 214. This aft portion defines a plurality of circumferential barbs 214a, and an end cap 202 is received on these barbs and is permanently engaged there by a matching set of inwardly extending barbs 202a. Slidably received in this body portion 112c is a one-piece molded hammer-and-sear member 184.

Preferably, this member 184 is molded of plastic polymer. The hammer-and-sear member 184 is seen in perspective in FIGS. 7 and 8. It is seen that this hammer-and-sear member 184 includes a cylindrical section 216 defining a spring recess 216a, into which the spring 192 is captively received and preloaded to make the device 110 ready for use. A center wall portion 218 of the member 184 provides a surface 218a, which is engageable with the gas capsule 182 to move this capsule forward, and to impale the capsule on the penetrator spike (not seen in FIG. 6, but recalling FIGS. 3–5 above). In order to hold the hammer-and-sear member against the pre-load of spring 192, and to resist the pressure of this spring over a long term the member 184 includes three axially extending legs 220.

Each of these legs 220 is a portion of a cone-shaped section 220a, best seen in FIGS. 7 and 8. The transition between the circular cylindrical section 216, and the cone-shaped section 220a is indicated with a dashed line circumscribing the member 184 in FIG. 7. Forwardly of this transition, the legs 220 flare out by their own resilience. As is seen in FIG. 6, these legs 220, at an end surface 220b of each one engage upon a ring-like abutment member 222 carried within the body portion 112c. As is best appreciated by consideration of FIG. 7, it is seen that the end surfaces 220b of the legs 220 are not formed on the radius of the cone-shape at this end of the member 184 (i.e., at the cone diameter having a center line indicated as "CL" on FIG. 7), but are formed at a smaller radius corresponding generally with the circular diameter of the section 216 (indicated by the radius lines and character "R" of FIG. 7). During storage of the device 110, these end surfaces 220b rest upon the abutment member 222 and transfer the spring force from spring 192 to this abutment member on a long-term basis.

In order to prevent creep of the plastic polymer material from which the member 184 is formed, the surfaces 220b define cooperatively, a contact area which corresponds substantially to that of the diameter 216 of the member 184 multiplied by the radial thickness of the legs 220. This contact surface area is sufficient to prevent creeping of the polymer from which the member 184 is formed.

In order to effect release of the hammer-and-sear member 184 when it is desired to effect a jet injection with the device 110, the body portion 112c defines three axially extending slots 200 (only one of which is seen in FIG. 6), each corresponding to a respective one of the legs 220. As is seen in FIG. 6, the trigger sleeve 122 carries three trigger blocks 122a (again, only one of which is seen in FIG. 6) which are slidably received in the slots 200. When this trigger sleeve 122 is moved forward, the trigger blocks 122a simultaneously force respective ones of the legs 220 radially inwardly and out of engagement with the abutment member 222, overcoming both the inherent resilience of these legs and the component of spring force resulting from the radial flaring of these legs. It will be appreciated that in view of this combination of inherent resilience and outward flare of the legs 220, there is virtually no risk that the device 110 will trigger except in response to deliberate forward movement of the trigger sleeve 122.

Because the legs 220 are formed at a circular (rather than conical) radius, they nest together and are received into the ring-like abutment member 222. Thus, the spring 192 forces the hammer-and-sear member 184 forcefully forward, effecting a jet injection from the device 110, as was explained above.

Figure 11:
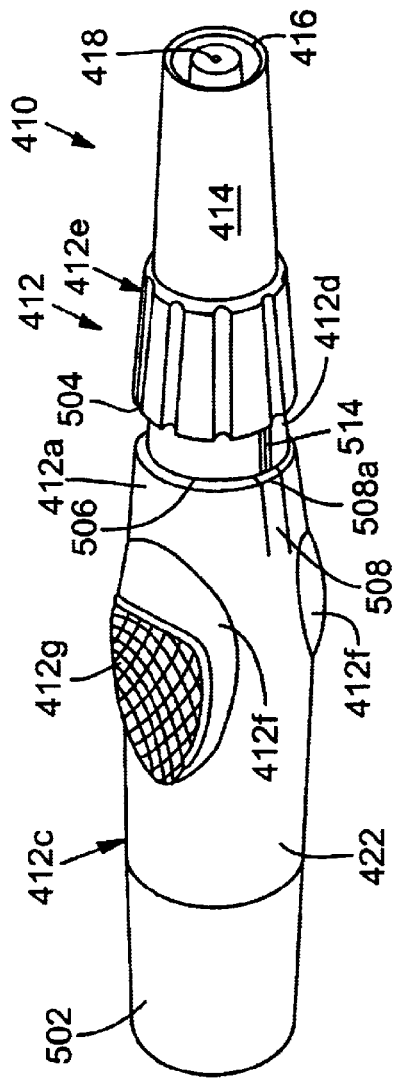
FIG. 11 is an exterior side perspective view of the injector device seen in FIG. 9, but with the device shown in an "inject" configuration preparatory to effecting a hypodermic jet injection.
Figure 12:
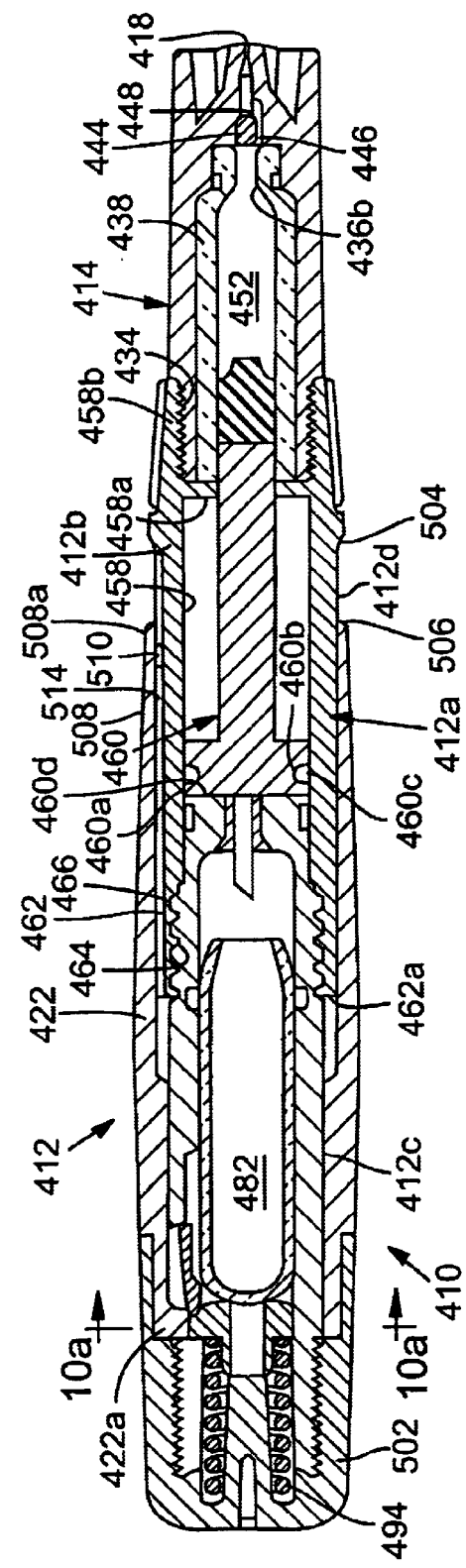
FIG. 12 is a longitudinal cross sectional view similar to FIG. 10, but shows the hypodermic jet injection device in the "inject" configuration prepatory to effecting a hypodermic jet injection.

Viewing now FIGS. 9–15, yet another alternative embodiment of a needle-free, hypodermic jet injection device is shown. Because the device illustrated in FIGS. 9–15 has many features that are the same as, or which are analogous in structure or function to those illustrated and described above, these features are indicated on FIGS. 9–15 using the same reference numeral used above, and increased by four-hundred (400). In FIGS. 9, 10, 10a, and 10b, the device 410 is shown in a storage condition. On the other hand, FIGS. 11, 12, and 12a show the device 410 in an "inject" condition preparatory to the effecting of a hypodermic jet injection using the device.

Viewing first FIGS. 9, 10, 10a and 10b, it is seen that the device 410 is in a storage configuration in which it is maintained until it is prepared for its use in administering an injection. The device 410 includes a hand piece assembly 412, preferably fabricated principally of injection molded plastic polymers, and including a pre-filled drug injection cartridge 414 with an end surface 416 at which is defined an injection orifice 418. The cartridge 414 has a glass sleeve 438, and an outlet orifice 436b, which is sealingly closed in the storage configuration of the device 410 by a plug 444.

In this embodiment, the plug 444 preferably takes the form of a ball member, forcibly and sealingly received into the outlet orifice 436b. This ball member 444 is more preferably formed of Teflon material (i.e., Polytetrafluoroethylene) in order to sealingly close the outlet orifice 436b, to provide a chemically inert plug member for the cartridge 414, and to facilitate a dependable and repeatable level of force required to dislodge this plug member from the orifice 436b. Importantly, viewing FIG. 10, it is seen that the cartridge 414 also defines a plug-capture chamber 446 immediately outside of the outlet orifice 436b from the glass sleeve 438. Further to the discussion above, it will be appreciated that the plug capture chamber 446 provides a "bypass" passage for outward flow of the medication in the cartridge 414 around the plug member ball 444 when this ball is in this chamber. In this embodiment, the chamber 446 takes the form of a concave or spherical cavity having also a plurality of bypass passages 448 (only one of which is seen in the drawing Figures) allowing bypass flow of the liquid medication past the plug member 444 when this plug member is in the chamber 446.

Considering now the hand piece assembly 412 in greater detail, as shown in FIGS. 9–10b, it is seen that the body 412a generally is formed of two main cooperative tubular sections 412b and 412c, which are threadably engaged with one another to form the hand piece assembly 412. The forward tubular body section 412b defines a stepped through bore 458, a forward portion 458a of which opens at 458b forwardly on the body 412, and which inwardly of this bore opening 458a defines the internal thread section 434 for threadably receiving the external threads on a drug cartridge (recalling the description above).

Sealingly and movably received in the bore portion 458a is a stepped injection piston member 460. A larger diameter portion 460a of this piston member defines a groove 460b carrying a seal member 460c sealingly engaging with the bore portion 458a to bound a gas pressure chamber 460d.

Again, considering the forward body section 412b in detail, it is seen that this body section defines a tubular aft body section 462 which has an axially disposed end surface 462a at which the stepped through bore 458 opens. Inwardly of this opening, the body section 462 defines an internal thread section 464 threadably engaging onto matching threads 466 of body section 412c. The body portion 412c carries a trigger sleeve 422, but the body portion 412b does not outwardly carry features like the projection 24, blocking pin 26, or recess 28 described above.

The present embodiment of injector 410 defines a pair of spaced apart axially disposed confronting annular surfaces 504, 506, one of which is defined on the forward body portion 412b, and the other of which is defined on the trigger sleeve 422. The surface 506 is interrupted by an axially extending resilient detent finger 508, the forward distal end portion 508a of which defines a radially inwardly extending nub 510. This radially inwardly extending nub 510 is removably received into a recess 512 defined in the radially outer surface of forward body portion 412c. The nub 510 and recess 512 have at least one sloping surface so that the body portions 412b and 412c can be relatively rotated manually from the position seen in FIG. 9 to that of FIG. 11 in the direction of the arrows of FIG. 9. Because of the at least one sloping surface on the recess 512 and/or nub 510, in response to this relative rotation of the body portions 412b and 412c (recalling that body portion 412c rotates in unison with trigger sleeve 422), it is seen that the detent finger 508 is forced from the recess 512 and rides about a cylindrical outer surface portion 412d of body portion 412b as the portions 412b and 412c are relatively rotated. As FIG. 11 illustrates, upon the two body portions 412b and 412c having been relatively rotated through about 180°, the nub 510 falls (actually "snaps") into an axially extending guide groove 514 defined by body portion 412b so that reverse relative rotation of the body portions 412b and 412c is resisted.

However, as will be seen, the nub 510 and guide groove 514 in cooperation with detent finger 508 serve both as a detent feature, and also serve as visual and auditory indicators of the condition of the device 440. That is, in condition of FIG. 9, the finger 508 is not aligned with the guide groove 514 and gives the impression that the trigger sleeve is not ready to move forward. On the other hand, in the condition of FIG. 11, the detent finger is aligned with the guide groove 514 and it appears that the trigger sleeve can be moved forward along this guide groove (which is true). Also, as the trigger sleeve is rotated from the position of FIG. 9 to that of FIG. 11, the detent finger provides an audible "snap" or "click" sound as the nub 510 drops into the guide groove 514. This "snap" sound is an indication to the user of the device 410 that it is ready to effect an injection.

In order to provide for improved manual purchase or grip upon the body 412, the forward portion 412b includes a radially outer and axially extending section 412c which provides surface roughening for better manual purchase in rotating the portions 412b and 412c relative to one another. In this case, the surface roughening is provided by plural ribs or lands and grooves alternating with one another as is depicted in FIG. 9. Similarly, the body 412 at aft portion 412c on trigger sleeve 422 provides a pair of diametrically opposed plateaus 412f, which are also provided with surface roughening 412g for better manual purchase. In this case, the surface roughening 412g is provided by knurling. Because of the diametrically opposed positions of the plateaus 412f on the body 412, the trigger sleeve 422 is particularly well grasped with the opposed thumb and index fingers. Thus is manual grasping and relative rotation of the body portions 412b and 412c (carrying trigger sleeve 422) effected. Also, thus is provided structure for an intuitive grasping of the device 410 by the user of the device, between the user's thumb and opposed index fingers, so that the trigger sleeve is used to position the device, and is then moved forwardly to effect an injection.

On the other hand, it is seen that the detent finger 508, recess 512, and guide groove 514 do not positively prevent reverse relative rotation of the body portions 412b and 412c from the position seen in FIG. 11 back to the position seen in FIG. 9. The same is true with respect to reverse relative rotation of the body portions from their positions seen in FIG. 9 in a direction opposite to the arrow of this FIG. (i.e., nub 510, recess 512, and guide groove 514 are merely detent, as well as visual and auditory indicator features).

Viewing FIG. 10b, it is seen that in order to cooperatively permit unidirectional relative rotation of the body portions 412b and 412c from their position of FIG. 9 to the position of FIG. 11, the body portion 412b includes an axially extending protrusion 516, which is adjacent to a helical end surface portion 518. Recalling the description above, it will be recalled that the body portion 412b defines an end surface 462a upon which the bore 458 opens. Thus, it is seen that the helical surface portion 518 is a part of end surface 462a. The trigger sleeve 422 defines a radially inwardly and axially extending key portion 520, which includes an angulated end surface portion 520a. In the relative position of body portions 412b and 412c seen in FIG. 9, the protrusion 516 engages against key portion 520 (as is illustrated in FIG. 10b) so that the body portions 412b and 412c can be relatively rotated only in the direction of the arrows seen in this Figure (which is the same relative rotation illustrated by the arrows of FIG. 9). In the relative position of FIG. 9, the angulated end surface 520a of the key 520 bears against the helical end edge surface portion 518 so that the trigger sleeve 422 cannot be moved forwardly from the storage position seen in FIG. 9. That is, the relatively large bearing area provided by the end edge surface 520a of the key 520 is sufficient to resist even attempts to manually force or jam the trigger sleeve 422 forwardly.

On the other hand, it is easily understood that the body portions 412b and 412c can be manually rotated from the relative position of FIG. 9 to that of FIG. 11. As this unidirectional relative rotation of the body portions 412b and 412c proceeds, the angulated end surface 520a of key 520 tracks along the helical surface 518 because this surface has the same pitch as the threads 464 and 466 (see FIG. 10b and 12a). In the position of FIG. 11, as is illustrated by FIG. 12a, the key 520 comes into contact with a circumferentially disposed step 462b on the body portion 412b. In this relative position of the body portion 412b and trigger sleeve 422, the key 520 is now in axial alignment with an axially extending keyway recess 522 defined by the body portion 412b. Thus, the trigger sleeve 422 could be moved forwardly relative to the body 412 to effect a jet injection with the injector 410.

However, in order to insure that the trigger sleeve 422 in not moved forwardly inadvertently by a user of the device 410, the device 410 includes an axial-movement resistance feature effective to prevent movement of the trigger sleeve 422 too easily in the axial forward direction, as well be further described below.

First, however, in order to complete this description of the device 410, attention now to FIGS. 9–15, and especially FIGS. 13 and 14 will show that the device includes a tabular and cylindrical hammer assembly 484. This hammer assembly 484 includes a ring-like sear carrier member 484a, and a hammer/spring seat member 486 which includes an annular spring seat surface 486a, a forwardly disposed axially surface 486b engageable both with the ring like member 484a and with the pressurized gas capsule 482, and also defines three radially extending sear pocket portions 488 each defining an axially disposed sear pocket 488a. In this embodiment, the capsule 482 preferably contains a pressurized gas, and most preferably contains pressurized nitrogen gas. A seal member 482a is carried by the body portion 412, and sealingly and movably cooperates with the capsule 482.

The ring-like member 484a includes three circumferentially arrayed and axially extending sear struts 490, which in the position of the hammer assembly seen in FIG. 10 rest at one end in a respective one of the sear pockets 488a. At the opposite end, each of these sear struts rests in a respective one of three catch recesses 492 inwardly defined by body portion 412c, viewing FIGS. 10 and 14. The sear struts 490 are pivotally connected to the ring-like member 484a by respective integral frangible living hinge sections 490a. These frangible hinge sections 490a are fractured during assembly of the device 410 so that the device is positively a single-use device. Further, the device 410 includes a spring 494 urging hammer assembly 484 forwardly. An end cap 502 captures the spring 494 and the hammer assembly 484 in the aft portion of the hand piece 412. The end cap 502 includes an axially elongate recoil buffer nose 502a, extending toward the hammer member 486. Similarly, the hammer member 486 includes a tubular recoil buffer portion 486b extending axially toward the nose portion 502a of the end cap 502.

Further, by comparing the illustration of FIG. 13 with that of FIG. 14, it may be seen in FIG. 13 that the ring like portion 484a is disposed relatively close axially to the aft end of the struts 490. On the other hand, the axial depth of the pockets 488a on hammer member 486 is greater than the axial projection of the struts 490 aft of the ring-like portion 484a. Consequently, when the device 410 is assembled, the surface 486b of the hammer member 486 engages the ring-like member 484a well before the aft end of the struts 490 are seated completely in sear pockets 488a (although the sear members are received partially into these pockets so as to guide the sear members). However, as the end cap 502 is threaded onto body section 412c, the spring force applied via spring 494 becomes sufficient to fracture the hinge sections 490a, allowing the sear members 490 to seat completely into the pockets 488a (i.e., resulting in the relative positions of these parts seen in FIGS. 10 and 12).

FIG. 14 illustrates the hammer and sear structure described above immediately after the moment of sear release (i.e., a split second before effecting of a hypodermic jet injection by use of the device 410). In this illustration of FIG. 14, it is seen that the trigger sleeve 422 has been moved forwardly sufficiently (indicated by the axially directed arrows in FIG. 14) that the trigger block portions 422a have dislodged the forward end of the sear struts 490 from their repose in catch recesses 492. Consequently, the hammer assembly 484 has started forward toward the gas capsule 482, and a jet injection will be effected when the pressurized gas within this capsule is utilized, as has been described above.

Turning now to FIG. 10a and FIG. 14a, it is seen that the trigger sleeve 422 defines three radially inwardly extending trigger blocks 422a. These trigger blocks 422a are slidably received into respective axially extending slots 500 defined by the body portion 412c. As FIG. 14a illustrates, the trigger blocks 422a are preferably provided with a fillet 422b at the radially outer intersection of these trigger blocks with the remainder of trigger sleeve 422. On the other hand, the adjacent portion of housing 412c (i.e., along the radially outer edge of the slots 500) is not provided with a matching "round," but instead has a comparatively sharp edge 524. This sharp edge 524 engages against the fillet 422b to frictionally resist axial-movement of the trigger sleeve 422 relative to the body portion 412c until a sufficient axial force has been applied by a user of the device 410. Once this threshold value of axial force has been applied by the user of the device 410, the trigger sleeve 422 slides forward to effect a jet injection, as has been described. Most preferably, the interference relationship of the trigger blocks 422a with the fillets 422b is provided only for an initial portion of the forward firing movement of the trigger sleeve 422. After the trigger sleeve 422 is moved forwardly through this initial interference distance, the interference force requirement is discontinued, and the axial force required on the trigger sleeve 422 in order to dislodge the struts 490 then provides some resistance to the movement of the trigger sleeve until the struts 490 are dislodged, and the device 410 discharges. The threshold level of axial force required of a user on the trigger sleeve 422 in order to effect initial axial movement of this trigger sleeve insures that the trigger sleeve does not move forward inadvertently, and also insures that when the user moves this trigger sleeve forward, it is a deliberate action and is because the user is ready and intends to effect a jet injection using the device 410. Further, this selected resistance to forward motion of the trigger sleeve 422 insures that the device 410 is pressed against the skin of the person who is to receive the jet injection with a selected level of axial force. That is, the surface 416 is most preferably pressed against the skin of the recipient of the jet injection with an axial force of about 3 to 4 pounds. This level of axial force is such that it provides the optimal degree of pressure of the surface 416 on the skin of the recipient, stretching the skin just sufficiently to insure an optimal jet injection, and insuring that the surface 416 of the injector 410 maintains contact with the skin during the brief interval of the injection.

The device 410 has a condition as seen in FIG. 15 for a relatively short interval during an injection, and it will be appreciated that pressurized gas from the capsule 482 (communicated to chamber 460b) is also effective to urge the capsule 482 rearwardly (leftwardly, as seen in FIG. 15). Consequently, the capsule 482 will recoil leftwardly from the position seen in FIG. 15 back toward its position of FIGS. 10 and 12. If the capsule 482 were allowed to recoil leftwardly a distance sufficient to move leftwardly of the seal 482a, then pressurized gas would be vented form the device 410. In order to prevent this venting of pressurized gas, the recoil buffer portions 486b and 502a confront and contact one another. Consequently, the capsule is stopped in its leftward recoil motion at the position of this capsule illustrated in FIGS. 10 and 12.

FIGS. 16–18 show a variation of injector 410, which is identified generally with the numeral 610. As in the prior figures, FIGS. 16–18 show injector 610 in "stored", "primed" and "fired" positions, respectively. In the stored configuration of FIG. 16, in which injector 610 is maintained until it is prepared for use, the gas capsule 682 is spaced from penetrator spike 678. Pre-filled drug injection cartridge 614 is closed at the injection end by ball member 644 which, like ball member 444, is typically spherical in configuration and is fabricated of polytetrafluoroethylene ("ptfe") or some other chemically inert material.

FIG. 17, depicting the "primed" configuration, shows that the ball member 644 has been shifted to the forward position within plug capture chamber 646. This is effected by rotating body portion 612b with respect to portion 612c. As described earlier in the discussion of injector 410, the threading between portions 412b and 412c moves the plunger 650 slightly forwardly, thus exerting a forward force on ball member 644 to move it to its position within chamber 646. As in device 410, chamber 646 provides a bypass passage for outward flow of medication from cartridge 614 and around ball member 644.

FIG. 18 shows injector 610 after the device has been fired and the medication has passed around ball member 644 and through chamber 646 and out orifice 636b and into the patient.

The construction and operation of injector 610 is virtually identical to injector 410, except that capsule 682 is shown to be in abutment with and actually engaged by or affixed to hammer member 684. In one preferred embodiment this affixation is by adhesive, but it is possible that other means, such as mechanical clamps, may be utilized. A mounting pad 685 is disposed at the forward end of hammer member 684 to provide an adherence face to which capsule 682 is adhered. The advantage of this configuration is that hammer member 684 and capsule 682 act as a unit. The mounting pad 685 is depicted as being concave in order to maximize the adherence between the pad and capsule 682.

Injection is effected as described above with respect to injector 410. In this embodiment a spring 692 is utilized to drive hammer member 684 and capsule 682 forwardly to be impaled on penetrator spike 678. This spring 692 is an example of what might be called a biasing system for providing the forward driving force. The biasing system might alternatively be in the form of another gas capsule or a cap or any other conventional system for providing such force. One difference in the depicted embodiment is that because capsule 682 is affixed to hammer member 684 and therefore travels with it, the mass of these two members is added together to provide additional energy which drives penetrator spike 678 more quickly and more completely into penetrable wall 682d.

Another difference with respect to injector 610 is that hollow penetrator spike 678 is cut at a 45° angle for reasons which will be explained more fully below. The outer diameter of spike 678 is normally approximately 0.080 inch and the inner diameter is normally approximately 0.060 inch.

Figure 20:
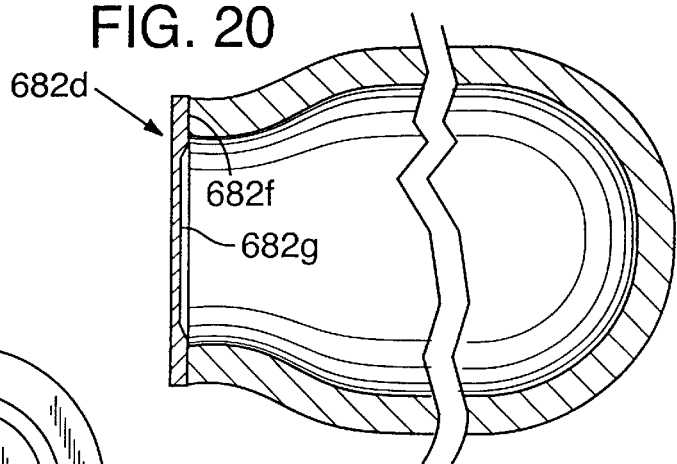
FIG. 20 is an enlarged, fragmentary side elevation view of the gas capsule penetrable wall.
Figure 21:
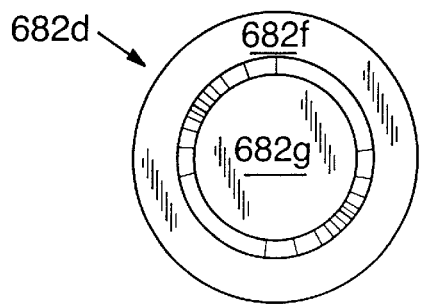
FIG. 21 is an enlarged front elevation view of the gas capsule penetrable wall.

Yet another difference in injector 610 is depicted in FIGS. 20 and 21. These figures show that wall section 682d includes a thickened section (sometimes called a first portion) 682f and an easily pierced or thinner section 682g. Thickened section 682f is adjacent the radial outer portion of wall section 682d, and thinner section 682g is at the radially inner portion, in a round configuration concentric with the round thickened section. Easily pierced or thinner section 682g is normally approximately 0.100 in diameter. This is to ensure that spike 678 contacts the thinner section 682g as relative movement is effected between the spike and wall section 682d. In fact, the difference between the outer diameter of spike 678 and the diameter of thinner section 682g provides a margin of safety so the spike will not have to cut through any portion of thickened section 682f.

Figure 22:
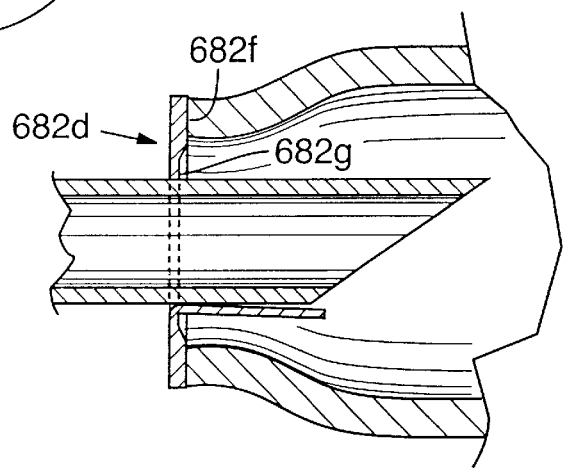
FIG. 22 is an enlarged, fragmentary side elevation view of the gas capsule penetrable wall after it has been pierced by the penetrator spike.

The increased mass of hammer member and capsule 682 moving in unison combines with the very effective 45° configuration of penetrator spike 678 and the thinner portion 682g of penetrable wall 682d to provide a quick and virtually complete cut through the penetrable wall. Specifically, in some prior art designs the spike wall only cuts a portion of the penetrable wall before the gas pressure begins surging through. So, for example, if only 220° of cut is made prior to the pressure being released, the escaping gas will be obstructed by the remaining 140°, and the flapping of the 220° which has been cut through. As shown best in FIG. 22, the cut in this preferred embodiment is virtually complete so that as much as 350° of the circular or round cut has been made before the gas is released. This minimizes the obstruction and the flapping, and ensures an immediate pressure increase (as described below in the discussion of FIG. 19), thereby promoting an effective injection of injectate through the skin of the patient. This is far preferable to a slower elevation in pressure which might result in the event of a less than virtually complete cutting of penetrable wall 682d. A slower elevation in pressure might result in insufficient penetration of injectate or could even result in momentary splash back prior to the point at which the pressure is sufficient to penetrate the skin.

Figure 23:
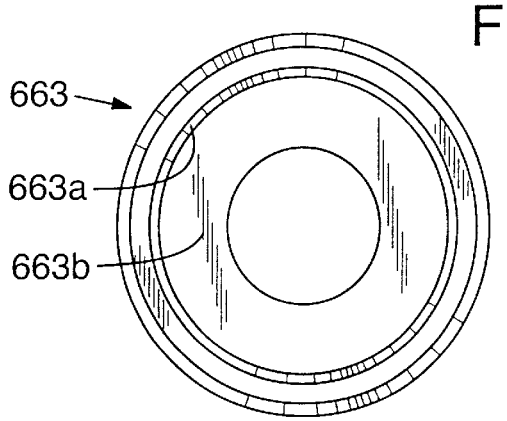
FIG. 23 is an end elevation view of the V-shaped seal member, taken from the perspective of 23—23 in FIG. 24.
Figure 24:
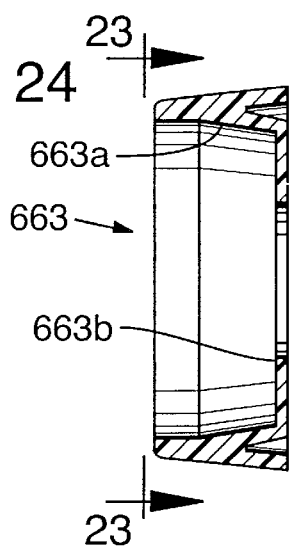
FIG. 24 is a side elevation sectional view of the V-shaped seal member depicted in the other figures.

A final difference between injectors 410 and 610 is the presence of a V-shaped seal which is shown best in FIGS. 23 and 24. These figures depict V-shaped seal member 663 which is mounted within injector 610 adjacent the tapered portion of gas capsule 682 (see FIGS. 23–24). As shown by comparing FIGS. 16–18, it can be seen that the V-shaped seal member 663 travels with capsule 682 as it is driven forwardly against penetrator spike 678 by spring 692 and hammer member 684. The V-shaped seal member 663 includes a V-shaped portion 663a (see FIGS. 16–18) which is designed to receive and withstand pressure forces which are imparted as capsule 682 is pierced. In fact, the pressure actually causes the seal to seal more tightly the region between the capsule and the inner wall of the injector. A flange 663b extends over a portion of the penetrable wall 682d and is typically fastened to wall 682d by adhesive to ensure that the V-shaped seal member 663 is engaged by and travels with capsule 682a, thereby providing an effective seal through the entire range of travel of the capsule. Specifically, flange 663b extends over at least a portion of the thickened portion 682f of penetrable wall 682d. Flange 663b does not, of course, extend over any portion of thinner section 682g of penetrable wall 682d. Seal member 663 is typically fabricated of a standard elastomer seal material as used in U-cups and O-rings.

Figure 19:
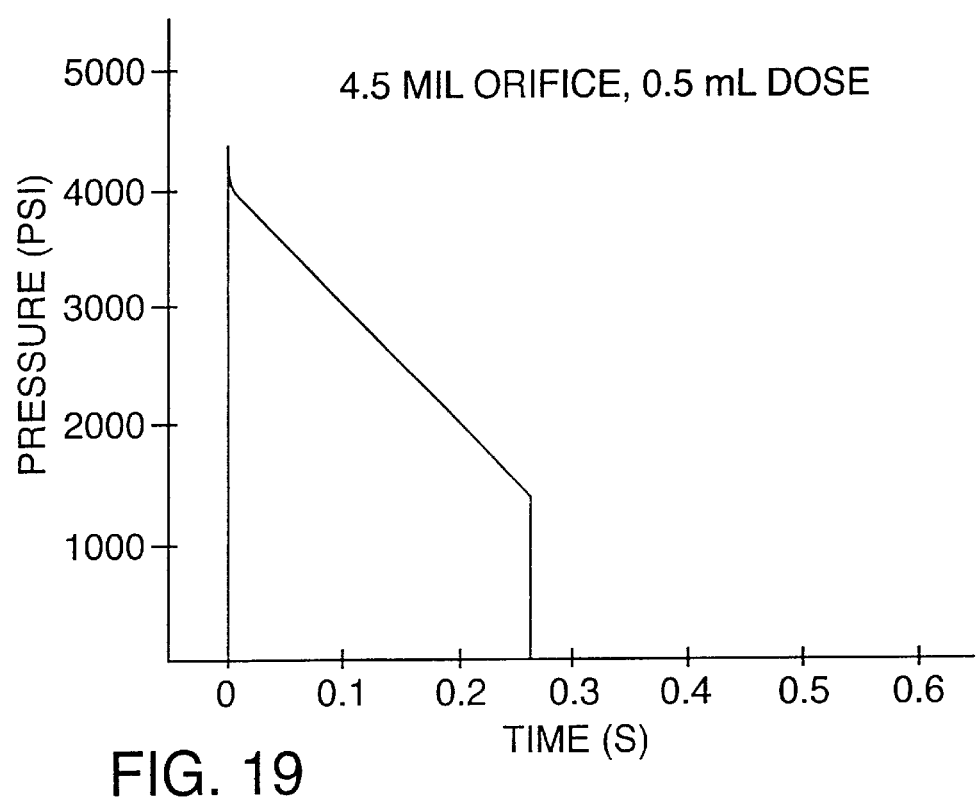
FIG. 19 is a graphic illustration of a pressure-time preferred injection pressure profile.

FIG. 19 depicts the preferred pressure-time curve which results from the immediate and virtually complete piercing of the penetrable wall 682b with the mechanism of injector 610 of FIGS. 16–18. FIG. 19 shows an immediate rise in pressure to approximately 2800 to 4200 psi, followed by a substantially linear drop off in pressure, followed by an abrupt cut off in pressure. In operation, the skin is pierced during the initial high pressure phase, thus ensuring skin penetration of any skin type, and with virtually any solution, with no splash back. The substantial linear drop off of pressure is more advantageous than a more abrupt but flattening pressure curve because this facilitates injection of increased amounts of injectate within the same time period. The abrupt cut off prevents splash back at the end of the injection process and ensures that the injectate is injected at the desired depth.

In the preferred embodiment nitrogen is used in the cartridge to provide the source of pressure. Nitrogen has more thermal stability than carbon dioxide and exhibits better leak control than helium. Typically the nitrogen is provided in the cartridge at a pressure of 1750 psi.

While the invention has been depicted and described by reference to several particularly preferred embodiments of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

We claim:

1. A needleless injector system comprising:
    an injector body member defining an inner chamber and an injection orifice;
        a gas capsule positioned within the body member chamber, the capsule having a penetrable wall at one end thereof;
        a capsule piercing member facing and spaced from the penetrable wall;
        a hammer member disposed in abutment with and affixed to the end of the capsule remote from the penetrable wall;
        a biasing system for selectively imparting a biasing force against the hammer member and the capsule; and
        a locking system for maintaining the piercing member spaced from the penetrable wall until the hammer member and the capsule are biased toward the piercing member.

2. The system of claim 1, wherein the hammer member is adhesively affixed to the capsule.

3. The system of claim 1 wherein the orifice is at a forward end of the injector body member and the penetrable wall is at a forward end of the capsule, with the hammer member disposed at a rearward end of the capsule.

4. The system of claim 1 wherein the biasing system for selectively imparting a biasing force comprises a spring member positioned at the rear end of the hammer member.

5. A needleless injector system comprising:
    an injector body assembly defining an inner chamber and an injection orifice;
        a gas capsule positioned within the body assembly chamber, the capsule having a penetrable wall at one end thereof;
        a capsule piercing member facing and spaced from the penetrable wall;
        the capsule being moveable relative to the injector body assembly;
        a hammer member disposed in abutment with and affixed to the capsule;
        a biasing system for selectively imparting a biasing force against the hammer member; and
        a locking system for maintaining the piercing member spaced from the penetrable wall until biasing force is imparted against the hammer member.

6. The injector system of claim 5 wherein the biasing system comprises a spring member positioned at the rear end of the hammer member.

* * * * *